United States Patent
Weingarten et al.

(10) Patent No.: US 9,848,953 B2
(45) Date of Patent: *Dec. 26, 2017

(54) DYNAMIC 3D LUNG MAP VIEW FOR TOOL NAVIGATION INSIDE THE LUNG

(71) Applicant: COVIDIEN LP, Mansfield, MA (US)

(72) Inventors: Oren P. Weingarten, Hod-Hasharon (IL); Ron Barak, Tel Aviv (IL)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,472

(22) Filed: Mar. 2, 2017

(65) Prior Publication Data

US 2017/0172664 A1 Jun. 22, 2017

Related U.S. Application Data

(63) Continuation of application No. 14/751,257, filed on Jun. 26, 2015, now Pat. No. 9,603,668.

(60) Provisional application No. 62/020,262, filed on Jul. 2, 2014.

(51) Int. Cl.
| G06K 9/00 | (2006.01) |
| A61B 34/10 | (2016.01) |
| G06T 19/00 | (2011.01) |
| G06T 7/00 | (2017.01) |

(52) U.S. Cl.
CPC ............ A61B 34/10 (2016.02); G06T 7/0012 (2013.01); G06T 19/003 (2013.01); *A61B 2034/105* (2016.02); *A61B 2034/107* (2016.02); *G06T 2207/30064* (2013.01); *G06T 2210/41* (2013.01)

(58) Field of Classification Search
None
See application file for complete search history.

(56) References Cited

U.S. PATENT DOCUMENTS

| 5,592,939 A | 1/1997 | Martinelli |
| 5,611,025 A | 3/1997 | Lorensen et al. |
| 5,676,673 A | 10/1997 | Ferre et al. |
| 5,697,377 A | 12/1997 | Wittkampf |
| 5,699,799 A | 12/1997 | Xu et al. |
| 5,715,836 A | 2/1998 | Kliegis et al. |
| 5,729,129 A | 3/1998 | Acker |
| 5,752,513 A | 5/1998 | Acker et al. |
| 5,782,762 A | 7/1998 | Vining |
| 5,881,124 A | 3/1999 | Giger et al. |
| 5,891,030 A | 4/1999 | Johnson et al. |

(Continued)

*Primary Examiner* — Tahmina Ansari

(57) ABSTRACT

A method for implementing a dynamic three-dimensional lung map view for navigating a probe inside a patient's lungs includes loading a navigation plan into a navigation system, the navigation plan including a planned pathway shown in a 3D model generated from a plurality of CT images, inserting the probe into a patient's airways, registering a sensed location of the probe with the planned pathway, selecting a target in the navigation plan, presenting a view of the 3D model showing the planned pathway and indicating the sensed location of the probe, navigating the probe through the airways of the patient's lungs toward the target, iteratively adjusting the presented view of the 3D model showing the planned pathway based on the sensed location of the probe, and updating the presented view by removing at least a part of an object forming part of the 3D model.

20 Claims, 7 Drawing Sheets

(56) References Cited

U.S. PATENT DOCUMENTS

| | | |
|---|---|---|
| 5,913,820 A | 6/1999 | Bladen et al. |
| 5,920,319 A | 7/1999 | Vining et al. |
| 5,967,980 A | 10/1999 | Ferre et al. |
| 5,971,767 A | 10/1999 | Kaufman et al. |
| 5,987,960 A | 11/1999 | Messner et al. |
| 6,019,725 A | 2/2000 | Vesely et al. |
| 6,047,080 A | 4/2000 | Chen et al. |
| 6,083,162 A | 7/2000 | Vining |
| 6,138,045 A | 10/2000 | Kupinski et al. |
| 6,151,404 A | 11/2000 | Pieper |
| 6,167,296 A | 12/2000 | Shahidi |
| 6,181,348 B1 | 1/2001 | Geiger |
| 6,201,387 B1 | 3/2001 | Govari |
| 6,233,476 B1 | 5/2001 | Strommer et al. |
| 6,246,784 B1 | 6/2001 | Summers et al. |
| 6,266,551 B1 | 7/2001 | Osadchy et al. |
| 6,332,089 B1 | 12/2001 | Acker et al. |
| 6,346,940 B1 | 2/2002 | Fukunaga |
| 6,366,800 B1 | 4/2002 | Vining et al. |
| 6,381,485 B1 | 4/2002 | Hunter et al. |
| 6,387,092 B1 | 5/2002 | Burnside et al. |
| 6,466,815 B1 | 10/2002 | Saito et al. |
| 6,496,188 B1 | 12/2002 | Deschamps et al. |
| 6,501,848 B1 | 12/2002 | Carroll et al. |
| 6,501,981 B1 | 12/2002 | Schweikard et al. |
| 6,505,065 B1 | 1/2003 | Yanof et al. |
| 6,522,907 B1 | 2/2003 | Bladen et al. |
| 6,526,162 B2 | 2/2003 | Asano et al. |
| 6,535,756 B1 | 3/2003 | Simon et al. |
| 6,578,579 B2 | 6/2003 | Burnside et al. |
| 6,584,174 B2 | 6/2003 | Schubert et al. |
| 6,603,868 B1 | 8/2003 | Ludwig et al. |
| 6,611,793 B1 | 8/2003 | Burnside et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,505,809 B2 | 3/2009 | Strommer et al. |
| 7,517,320 B2 | 4/2009 | Wibowo et al. |
| 7,518,619 B2 | 4/2009 | Stoval, III et al. |
| 7,630,752 B2 | 12/2009 | Viswanathan |
| 7,630,753 B2 | 12/2009 | Simon et al. |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 * | 7/2010 | Odry .................. G06K 9/4638 382/131 |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gundel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 * | 10/2012 | Cohen .................. A61B 5/0044 382/128 |
| 8,298,135 B2 | 10/2012 | Ito et al. |
| 8,391,952 B2 | 3/2013 | Anderson |
| 8,417,009 B2 | 4/2013 | Mizuno |
| 8,494,612 B2 | 7/2013 | Vetter et al. |
| 8,509,877 B2 | 8/2013 | Mori et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |
| 8,798,339 B2 | 8/2014 | Mielekamp et al. |
| 8,801,601 B2 | 8/2014 | Prisco et al. |
| 8,819,591 B2 | 8/2014 | Wang et al. |
| 8,862,204 B2 | 10/2014 | Sobe et al. |
| 9,008,754 B2 * | 4/2015 | Steinberg ............. A61B 5/0044 600/407 |
| 9,603,668 B2 | 3/2017 | Weingarten et al. |
| 2005/0207630 A1 * | 9/2005 | Chan ...................... A61B 6/466 382/131 |
| 2008/0183073 A1 | 7/2008 | Higgins et al. |
| 2009/0012390 A1 | 1/2009 | Pescatore et al. |
| 2009/0030306 A1 | 1/2009 | Miyoshi et al. |
| 2010/0290693 A1 * | 11/2010 | Cohen .................. A61B 5/0044 382/134 |
| 2010/0310146 A1 | 12/2010 | Higgins et al. |
| 2010/0312094 A1 | 12/2010 | Guttman et al. |
| 2011/0237897 A1 | 9/2011 | Gilboa |
| 2011/0251607 A1 | 10/2011 | Kruecker et al. |
| 2012/0203065 A1 | 8/2012 | Higgins et al. |
| 2012/0249546 A1 | 10/2012 | Tschirren et al. |
| 2012/0280135 A1 | 11/2012 | Bal |
| 2012/0287238 A1 | 11/2012 | Onishi et al. |
| 2013/0165854 A1 | 6/2013 | Sandhu et al. |
| 2013/0317352 A1 * | 11/2013 | Case ........................ G06T 7/73 600/424 |
| 2015/0305612 A1 * | 10/2015 | Hunter ................... A61B 34/20 600/424 |
| 2016/0000302 A1 * | 1/2016 | Brown .................. A61B 6/032 600/103 |
| 2016/0005220 A1 * | 1/2016 | Weingarten ............. G06T 19/20 382/131 |

\* cited by examiner

DYNAMIC 3D LUNG MAP VIEW FOR TOOL NAVIGATION INSIDE THE LUNG

CROSS-REFERENCE TO RELATED APPLICATIONS

The present application is a continuation of U.S. patent application Ser. No. 14/751,257, filed on Jun. 26, 2015, and entitled "DYNAMIC 3D LUNG MAP VIEW FOR TOOL NAVIGATION INSIDE THE LUNG," which claims the benefit of and priority to U.S. Provisional Patent Application Ser. No. 62/020,262 filed on Jul. 2, 2014, the entire contents of which are incorporated herein by reference.

BACKGROUND

Technical Field

The present disclosure relates to the treatment of patients with lung diseases and, more particularly, to devices, systems, and methods for implementing a dynamic 3D lung map view for tool navigation inside a patient's lungs.

Description of Related Art

Lung cancer has an extremely high mortality rate, especially if it is not diagnosed in its early stages. The National Lung Screening Trial has demonstrated that a reduction in mortality occurs if diagnostic scans such as computed tomography (CT) scans are used for early detection for those at risk of contracting the disease. While CT scans increase the possibility that small lesions and nodules in the lung can be detected, these lesions and nodules still require biopsy and cytological examination before a diagnosis can be rendered and treatment can be undertaken.

To perform a biopsy, as well as many treatments, navigation of tools within the lungs to the point of biopsy or treatment is necessary. Accordingly, improvements to systems and methods of navigating are continually being sought.

SUMMARY

Provided in accordance with the present disclosure is a method for implementing a dynamic three-dimensional (3D) lung map view for navigating a probe inside a patient's lungs.

In an aspect of the present disclosure, the method includes loading a navigation plan into a navigation system, the navigation plan including a planned pathway shown in a 3D model generated from a plurality of CT images, inserting the probe into a patient's airways, the probe including a location sensor in operative communication with the navigation system, registering a sensed location of the probe with the planned pathway, selecting a target in the navigation plan, resenting a view of the 3D model showing the planned pathway and indicating the sensed location of the probe, navigating the probe through the airways of the patient's lungs toward the target, iteratively adjusting the presented view of the 3D model showing the planned pathway based on the sensed location of the probe, and updating the presented view by removing at least a part of an object forming part of the 3D model.

In another aspect of the present disclosure, iteratively adjusting the presented view of the 3D model includes zooming in when the probe approaches the target.

In yet another aspect of the present disclosure, iteratively adjusting the presented view of the 3D model includes zooming in when the diameter of an airway within which the probe is sensed to be located is less than a predetermined threshold.

In another aspect of the present disclosure, iteratively adjusting the presented view of the 3D model includes changing the presented view to a view wherein the airway tree bifurcation is maximally spread.

In yet another aspect of the present disclosure, iteratively adjusting the presented view of the 3D model includes aligning the view with the sensed location of the probe to show where the probe is and what lies ahead of the probe.

In another aspect of the present disclosure, iteratively adjusting the presented view of the 3D model includes changing the presented view to be orthogonal to a vector from the probe to the pathway.

In yet another aspect of the present disclosure, iteratively adjusting the presented view of the 3D model includes changing the presented view to be perpendicular to the sensed location of the probe in relation to the 3D model to show the area around the probe.

In another aspect of the present disclosure, iteratively adjusting the presented view of the 3D model includes changing the presented view to be behind the sensed location of the probe in relation to the 3D model to show the area ahead of the probe.

In yet another aspect of the present disclosure, iteratively adjusting the presented view of the 3D model includes changing the presented view to be at the tip of the probe and orthogonal to the directing in which the probe is moving.

In another aspect of the present disclosure, iteratively adjusting the presented view of the 3D model includes changing the presented view to be perpendicular to a vector from the probe to the target to show the alignment of the probe to the target.

In yet another aspect of the present disclosure, iteratively adjusting the presented view of the 3D model includes rotating the presented view around a focal point to improve a 3D perception of the sensed location of the probe in relation to the 3D model.

In a further aspect of the present disclosure, updating the presented view by removing at least part of an object includes removing at least part of an object which is outside of a region of interest.

In yet a further aspect of the present disclosure, updating the presented view by removing at least part of an object includes removing at least part of an object which is obstructing the probe.

In a further aspect of the present disclosure, updating the presented view by removing at least part of an object includes removing at least part of an object which is obstructing the target.

In yet a further aspect of the present disclosure, updating the presented view by removing at least part of an object includes removing at least part of an object which is not relevant to the sensed location of the probe.

In a further aspect of the present disclosure, updating the presented view by removing at least part of an object includes removing at least part of an object which is not relevant to a current selected state of the navigation system.

In another aspect of the present disclosure, the method further includes presenting an alert.

In a further aspect of the present disclosure, presenting an alert includes presenting an alert when the probe is approaching the pleura.

In yet a further aspect of the present disclosure, presenting an alert includes presenting an alert when the tool is approaching major blood vessels.

In a further aspect of the present disclosure, presenting an alert includes presenting an alert when the sensed location of the probe is off of the planned pathway.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
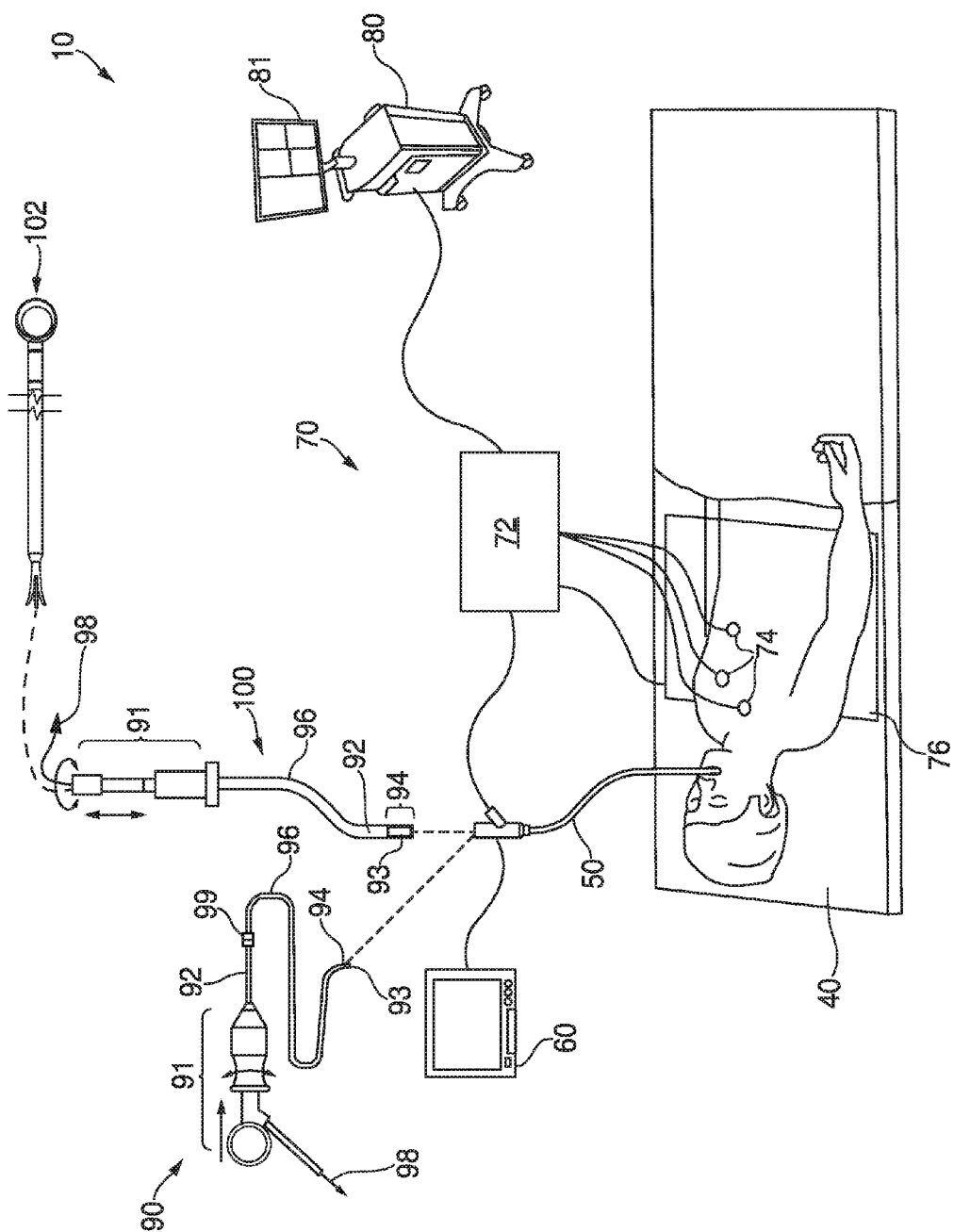
FIG. 1 depicts a system diagram of an example electromagnetic navigation (EMN) system which may be used to create and display a dynamic 3D lung map view, according to an embodiment of the present disclosure.

Devices, systems, and methods for implementing a dynamic 3D lung map view for tool navigation inside a patient's lungs are provided in accordance with the present disclosure. A location sensor may be incorporated into different types of tools and catheters to track the location and assist in navigation of the tools. The tracked location of the location sensor may be used to visually show the location of a tool on the dynamic 3D lung map. The location of the location sensor within the body of a patient, with reference to a 3D map or 2D images as well as a planned pathway assists the clinician in navigating lungs of the patient. However, because of the amounts of data being presented and the ability to show details of the airways, there is a desire to assist the clinician and eliminate unessential data or data regarding portions of the anatomy that are unrelated to a specific navigation or a specific procedure. In addition, there is a desire to harness this detailed anatomical data and alert the clinician regarding proximity to certain anatomical features. These and other aspects of the present disclosure are detailed herein below.

The dynamic 3D lung map view, as disclosed herein, is one of a variety of views that may be presented by an electromagnetic navigation (EMN) system which may be used by a clinician to perform an ELECTROMAGNETIC NAVIGATION BRONCHOSCOPY® (ENB) procedure. Among other tasks that may be performed using the EMN system are planning a pathway to target tissue, navigating a positioning assembly to the target tissue, and navigating a variety of tools, such as a locatable guide (LG) and/or a biopsy tool to the target tissue.

An ENB procedure generally involves at least two phases: (1) planning a pathway to a target located within, or adjacent to, the patient's lungs; and (2) navigating a probe to the target along the planned pathway. These phases are generally referred to as (1) "planning" and (2) "navigation." An example of the planning software described herein can be found in U.S. patent application Ser. Nos. 13/838,805, 13/838,997, and 13/839,224, all of which are filed by Covidien LP on Mar. 15, 2013 and entitled "Pathway Planning System and Method," all of which are incorporated herein by reference. An example of the planning software can be found in commonly assigned U.S. Provision Patent Application No. 62/020,240 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB procedure.

The application may use the CT scan image data to generate a three-dimensional (3D) model of the patient's lungs. The 3D model may include, among other things, a model airway tree corresponding to the actual airways of the patient's lungs, and showing the various passages, branches, and bifurcations of the patient's actual airway tree. Additionally, the 3D model may include lesions, markers, blood vessels, and/or a 3D rendering of the pleura. While the CT scan image data may have gaps, omissions, and/or other imperfections included in the image data, the 3D model is a smooth representation of the patient's airways, with any such gaps, omissions, and/or imperfections in the CT scan image data filled in or corrected. As described in more detail below, the 3D model may be viewed in various orientations. For example, if a clinician desires to view a particular section of the patient's airways, the clinician may view the 3D model represented in a 3D rendering and rotate and/or zoom in on the particular section of the patient's airways. Additionally, during the navigation phase of an ENB procedure, while a tool is being navigated through the patient's airways, the clinician may want to have the presented view of the 3D model dynamically updated as the tool is navigated. Such a dynamic 3D lung map view is disclosed below.

Prior to the start of the navigation phase of an ENB procedure, the 3D model is registered with the actual lungs of the patient. One potential method of registration involves navigating a locatable guide into each lobe of the patient's lungs to at least the second bifurcation of the airways of that lobe. The position of the locatable guide is tracked during this registration phase, and the 3D model is iteratively updated based on the tracked position of the locatable guide within the actual airways of the patient's lungs. This registration process is described in commonly-owned U.S. Provisional Patent Application Ser. No. 62/020,220 entitled "Real-Time Automatic Registration Feedback", filed on Jul. 2, 2014, by Brown et al. With reference to FIG. 1, an EMN system 10 is provided in accordance with the present disclosure. One such EMN system is the ELECTROMAG- NETIC NAVIGATION BRONCHOSCOPY® system currently sold by Covidien LP. As shown in FIG. 1, EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware, such as an EMN application 81, used to facilitate pathway planning, identification of target tissue, and navigation to the target tissue.

FIG. 1 also depicts two types of catheter guide assemblies 90, 100. Both catheter guide assemblies 90, 100 are usable with the EMN system 10 and share a number of common components. Each catheter guide assembly 90, 100 includes a handle 91, which is connected to an extended working channel (EWC) 96. EWC 96 is sized for placement into the working channel of bronchoscope 50. In operation, a locatable guide (LG) 92, including an electromagnetic (EM) sensor 94, is inserted into EWC 96 and locked into position such that the sensor 94 extends a desired distance beyond the distal tip 93 of EWC 96. The location of EM sensor 94, and thus the distal end of EWC 96, within an electromagnetic field generated by the electromagnetic field generator 76 can be derived by the tracking module 72, and the workstation 80. Catheter guide assemblies 90, 100 have different operating mechanisms, but each contain a handle 91 that can be manipulated by rotation and compression to steer the distal tip 93 of LG 92 and EWC 96. Catheter guide assemblies 90 are currently marketed and sold by Covidien LP under the name SUPERDIMENSION® Procedure Kits, similarly catheter guide assemblies 100 are currently sold by Covidien LP under the name EDGE® Procedure Kits, both kits include a handle 91, EWC 96, and LG 92. For a more detailed description of the catheter guide assemblies 90, 100, reference is made to commonly-owned U.S. patent application Ser. No. 13/836,203 entitled "MICROWAVE ABLATION CATHETER AND METHOD OF UTILIZING THE SAME", filed on Mar. 15, 2013 by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, entitled "Wireless six-degree-of-freedom locator", filed on Dec. 14, 1998 by Gilboa, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes EMN application 81 where sensors 74 are used to calculate a patient coordinate frame of reference.

Also shown in FIG. 1 is a biopsy tool 102 that is insertable into catheter guide assemblies 90, 100 following navigation to a target and removal of LG 92. The biopsy tool 102 is used to collect one or more tissue sample from the target tissue. As detailed below, biopsy tool 102 is further configured for use in conjunction with tracking system 70 to facilitate navigation of biopsy tool 102 to the target tissue, and tracking of a location of biopsy tool 102 as it is manipulated relative to the target tissue to obtain the tissue sample. Though shown as a biopsy tool in FIG. 1, those of skill in the art will recognize that other tools including for example microwave ablation tools and others may be similarly deployed and tracked as the biopsy tool 102 without departing from the scope of the present disclosure.

Although the EM sensor 94 is described above as being included in LG 92 it is also envisioned that EM sensor 94 may be embedded or incorporated within biopsy tool 102 where biopsy tool 102 may alternatively be utilized for navigation without need of LG 92 or the necessary tool exchanges that use of LG 92 requires. A variety of useable biopsy tools are described in U.S. Provisional Patent Application Nos. 61/906,732 and 61/906,762 both entitled "DEVICES, SYSTEMS, AND METHODS FOR NAVIGATING A BIOPSY TOOL TO A TARGET LOCATION AND OBTAINING A TISSUE SAMPLE USING THE SAME", filed Nov. 20, 2013 and U.S. Provisional Patent Application No. 61/955,407 having the same title and filed Mar. 14, 2014, the entire contents of each of which are incorporated herein by reference and useable with the EMN system 10 as described herein.

During procedure planning, workstation 80 utilizes computed tomographic (CT) scan image data for generating and viewing a three-dimensional (3D) model of the patient's airways, enables the identification of target tissue on the 3D model (automatically, semi-automatically or manually), and allows for the selection of a pathway through the patient's airways to the target tissue. The 3D model may be presented on a display monitor associated with workstation 80, or in any other suitable fashion.

Using workstation 80, various views of the 3D model may be presented and may be manipulated by a clinician to facilitate identification of a target and selection of a suitable pathway through the patient's airways to access the target. For example, EMN application 81 may be configured in various states to display the 3D model in a variety of view modes. Some of these view modes may include a dynamic 3D lung map view, as further described below. For each view of the 3D model, the angle from which the 3D model is displayed may correspond to a view point. The view point may be fixed at a predefined location and/or orientation, or may be adjusted by the clinician operating workstation 80.

The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure.

Following procedure planning, a procedure may be undertaken in which the EM sensor 94, in conjunction with tracking system 70, enables tracking of EM sensor 94 (and thus the distal end of the EWC or the tool 102) as EM sensor 94 is advanced through the patient's airways following the pathway planned during the procedure planning phase.

Figure 2:
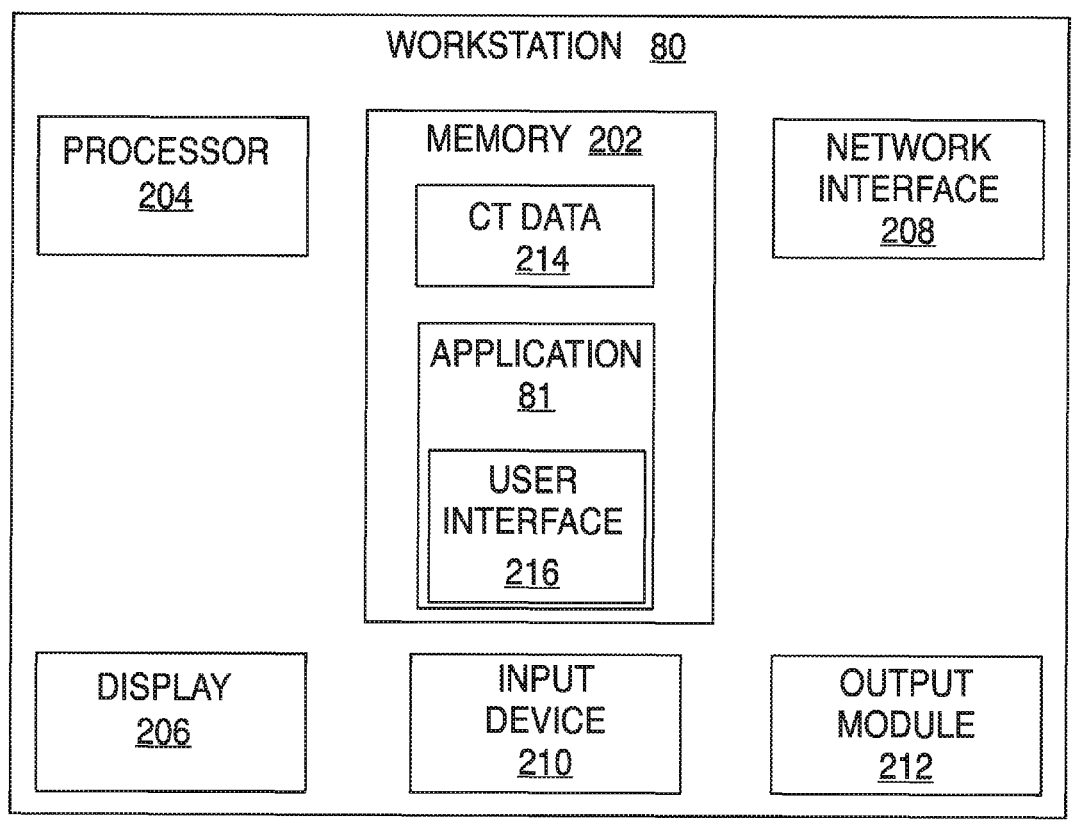
FIG. 2 depicts a schematic diagram of an example workstation forming part of the EMN system of FIG. 1 which may be used to create and display a dynamic 3D lung map view, according to an embodiment of the present disclosure.

Turning now to FIG. 2, there is shown a system diagram of workstation 80. Workstation 80 may include memory 202, processor 204, display 206, network interface 208, input device 210, and/or output module 212. Memory 202 may store EMN application 81 and/or CT data 214. EMN application 81 may, when executed by processor 204, cause display 206 to present user interface 216. The EMN application 81 provides the interface between the sensed position of the EM sensor 94 and the image and planning data developed in the planning phase.

Figure 3:
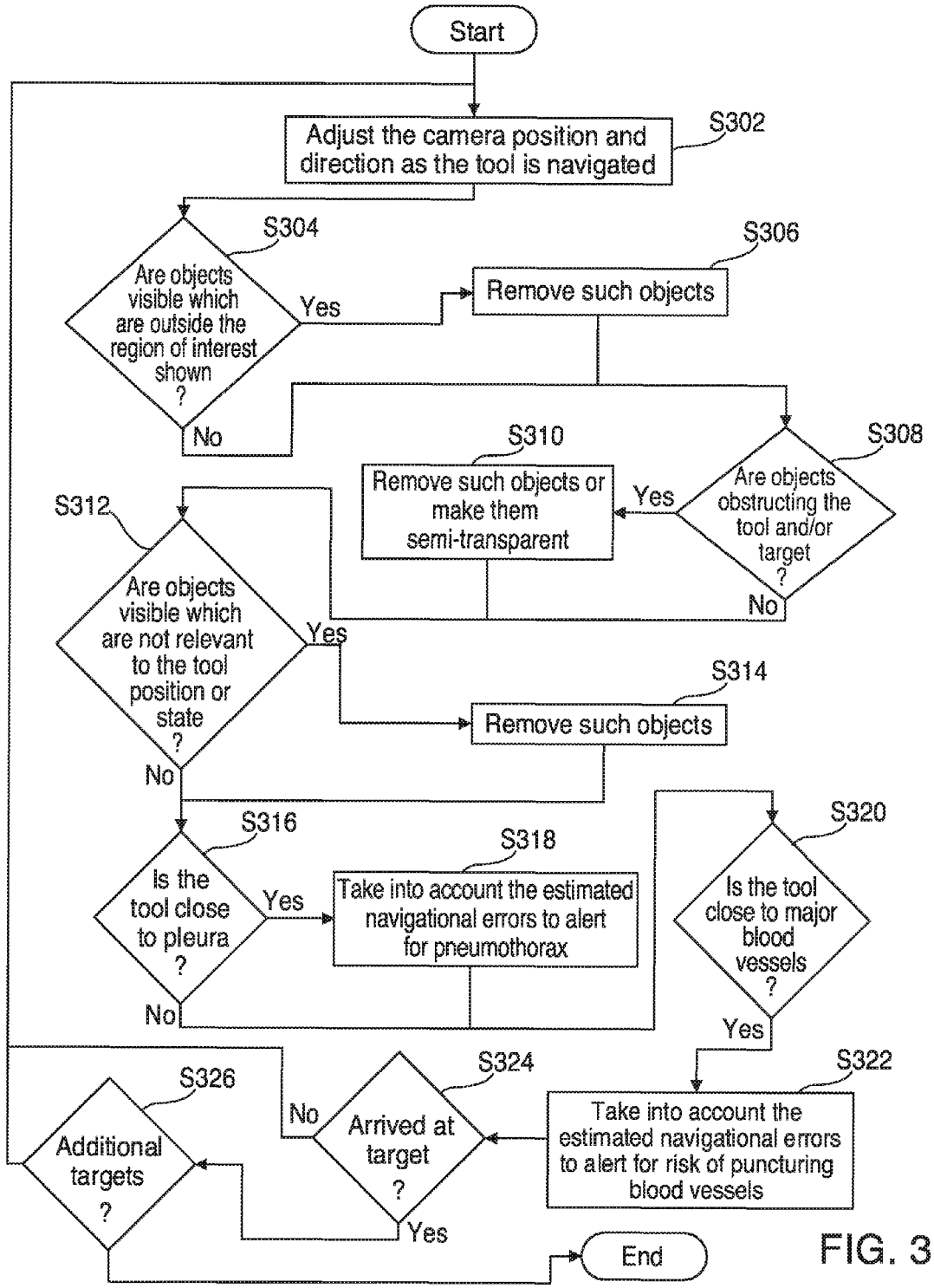
FIG. 3 is a flowchart illustrating an example method for creating a dynamic 3D lung map view, according to an embodiment of the present disclosure.
Figure 6:
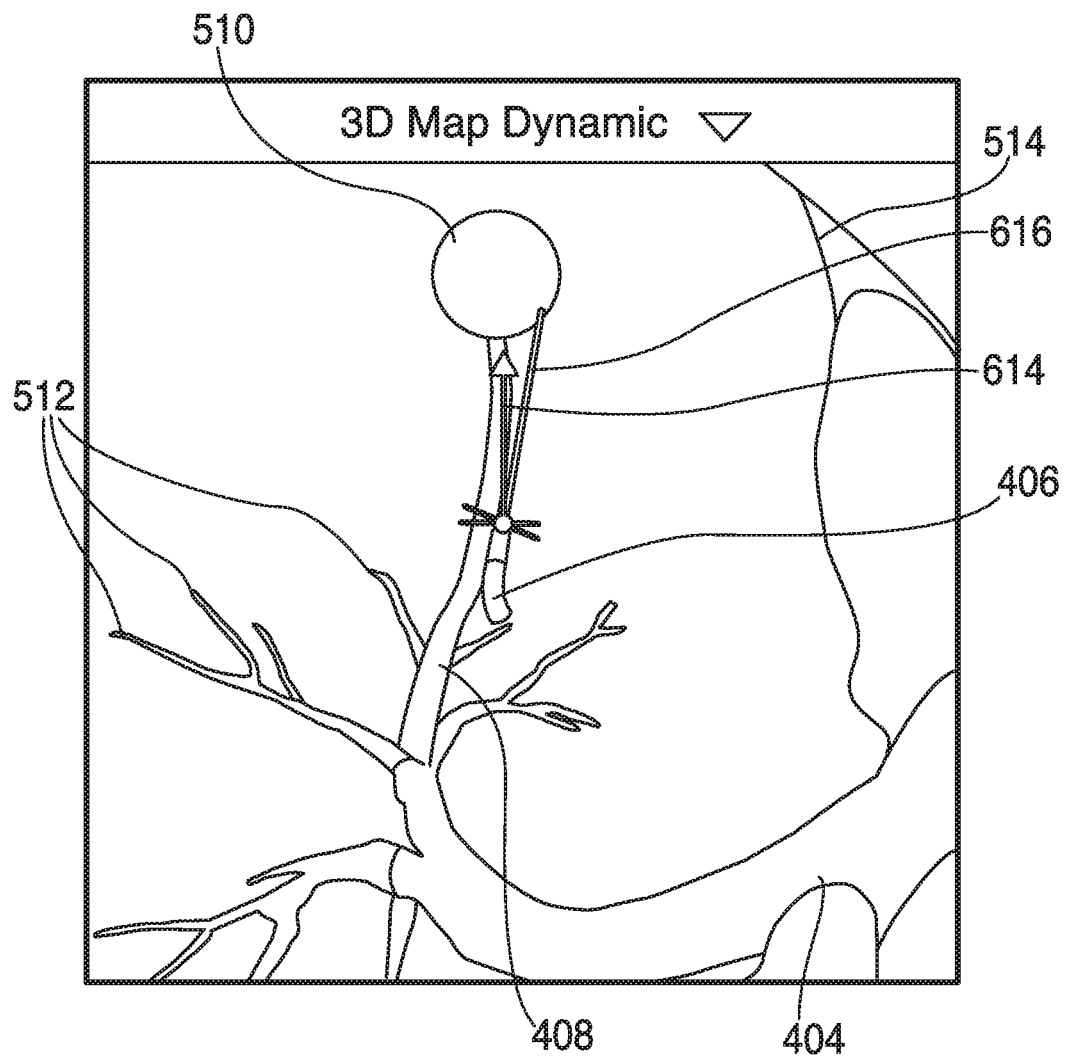
FIG. 6 illustrates an example of a dynamic 3D lung map view, according to an embodiment of the present disclosure.
Figure 7:
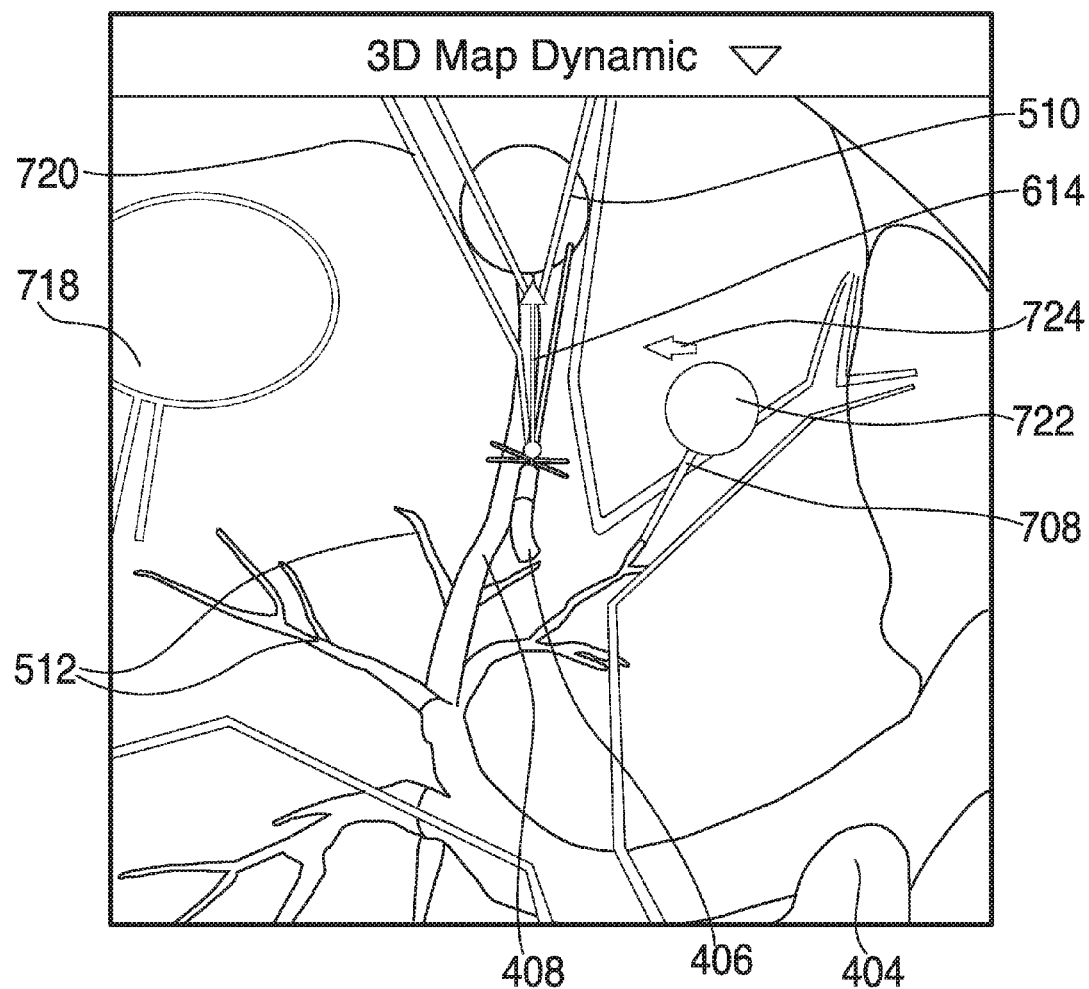
FIG. 7 illustrates another example of a dynamic 3D lung map view, according to an embodiment of the present disclosure.

Referring now to FIG. 3, there is shown an aspect which may be incorporated into an EMN application 81. Specifically, FIG. 3 depicts a flowchart of an exemplary method of creating a dynamic 3D lung map view. During an ENB procedure, this example method may be started when a clinician selects a dynamic 3D lung map view button 402 in an EMN application 81 user interface 400. Alternatively, button 402 may be a drop down menu from which the clinician may select the dynamic 3D lung map view from among a plurality of available views. Starting at step S302, the view point from which the 3D model is displayed may be automatically adjusted in relation to the tracked location of a tool, which is depicted as a probe 406 in FIGS. 4-7, inside the patient's lungs. Adjusting the view point may include moving the view point in relation to the 3D model and/or zooming in on the 3D model to display a closer image of the 3D model. As shown in FIG. 6 below, an unadjusted 3D lung map view (FIG. 5) is adjusted such that the position of a probe 406 is more clearly shown in relation to the position of a target 510 and surrounding airways 512. The view point may further be adjusted according to the direction in which probe 406 is being navigated and/or to be orthogonal to a vector between the tip of probe 406 and a target 510 or in relation to the pathway 408, as is shown in FIGS. 6 and 7, which depict the 3D model from a view point orthogonal to vector 614 which runs from the tip of digital probe 406 to target 510. The view point may further be adjusted by zooming in when probe 406 approaches target 510 or airways having a diameter less than a predetermined threshold. In an embodiment, a preferred view point may be such that the displayed view of the 3D model shows the bifurcations of the airway tree around digital probe 406 as maximally spread, that is, a view point from a direction showing the airway tree with as few overlapping branches as possible. In an embodiment the view point may be moved to be above probe 406 in relation to the 3D model, or behind probe 406 in relation to the 3D model, in order to provide the clinician with a clearer understanding of the position of probe 406 in relation to surrounding objects. In such an embodiment, the dynamic 3D lung map view may show the area of the 3D model in front of and around the tool, as shown in FIG. 7. In another embodiment, the view point may be moved such that the view presented by EMN application 81 is looking ahead out of the tip of digital probe 406.

Next, at step S304, EMN application 81 determines whether any objects are visible from the current view point but are outside of a region of interest for the current navigation procedure. An example might be other targets, or portions of the patient's physiology, such as blood vessels and the heart, which lie outside of the region in which the pathway is located, such as in other lobes of the patient's lungs, or along other branches of airway tree 404 which are not used for the current procedure. If EMN application 81 determines that such objects are visible, those objects may be removed from the view at step S306, as shown below by FIG. 7.

Thereafter, or if EMN application 81 determines that there are no such objects in the view, processing proceeds to step S308, where EMN application 81 determines whether there are objects obstructing the view of digital probe 406 and/or target 510. For example, depending on the angle of the view point, the surrounding airways which do not form part of the planned pathway may lie in the line of sight and between the view point and probe 406 or target 510. If EMN application 81 determines that such objects are obstructing the view of probe 406 or target 510, those objects may be removed from the view at step S310, as shown below by FIG. 7.

Thereafter, or if EMN application 81 determines that there are no such objects in the view, processing proceeds to step S312, where EMN application 81 determines if there are any objects visible in the view which are unrelated to the position of probe 406, the type of tool being used in the current navigation procedure, or the selected state of EMN application 81. For example, markers indicating the location of previous biopsies at different target locations may be within the view angle from the view point, but are not relevant to the current procedure, as shown below by FIG. 7. Another example may be targets 722 which are part of the current navigation plan but have at least one other target 510 which must be visited first. Such targets 722 may become visible or "unhidden" once target 510 has been visited and the necessary procedures performed. If EMN application 81 determines that such objects are within the view, those objects may be removed from the view at step S314.

Thereafter, or if EMN application 81 determines that there are no such objects in the view, processing proceeds to step S316, where EMN application 81 determines whether digital probe 406, and thus sensor 94, is approaching the pleural boundaries of the patient's lungs. EMN application 81 may determine that sensor 94 is approaching the pleural boundaries of the patient's lungs based on, for example, the distance between sensor 94 and the pleura, the angle between sensor 94 and the pleura, the speed at which sensor 94 is moving, and/or any combination thereof. The determination may further be based on a known or estimated rate of navigational errors. When sensor 94 is close to the pleura, there is an increased risk of injury, such as pneumothorax, to the patient, and the clinician may want to be aware of that to proceed with added caution. Thus, if EMN application 81 determines that sensor 94 is close to the pleura, EMN application 81 may present an alert to the clinician at step S318. EMN application 81 may also take known or estimated navigational errors into account when determining whether sensor 94 is approaching the pleura.

Thereafter, or if EMN application 81 determines that sensor 94 is not approaching the pleura, processing proceeds to step S320, where EMN application 81 determines whether sensor 94 is approaching one or more major blood vessels. As with the pleura, when sensor 94 is close to major blood vessels, particularly where a tool 102, such as a biopsy or microwave ablation tool, is being deployed, there is added risk of injury to the patient, and the clinician may want to be aware that sensor 94 is close to major blood vessels to proceed with added caution. Thus, if EMN application 81 determines that sensor 94 is close major blood vessels, EMN application 81 may present an alert to the clinician at step S322. Additionally, as with the pleura, EMN application 81 may take known or estimated navigational errors into account when determining whether sensor 94 is approaching major blood vessels.

Thereafter, or if EMN application 81 determines that sensor 94 is not approaching any major blood vessels, processing proceeds to step S324, where EMN application 81 determines whether probe 406 has arrived at the target. If EMN application 81 determines that probe 406 has not arrived at the target, processing returns to step S302. In this way, the dynamic 3D lung map view is continuously updated and/or adjusted during the navigation procedure. If EMN application 81 determines that digital probe 406 has arrived at the target, processing proceeds to step S326, where EMN application 81 determines whether there are more targets to be visited. If EMN application 81 determines that there are no more targets to be visited, processing ends. Otherwise, processing returns to step S302.

Figure 4:
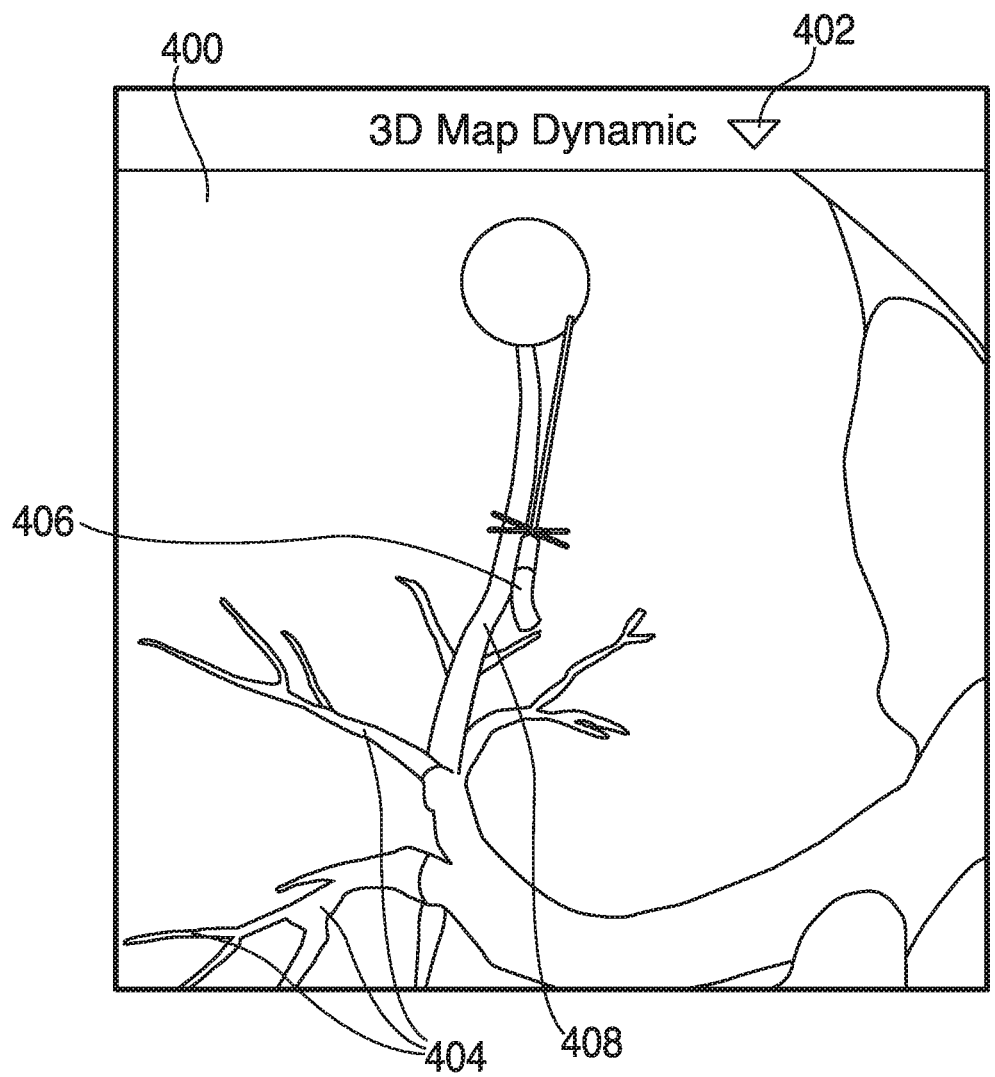
FIG. 4 illustrates an example view of a user interface that may be presented on the workstation of FIG. 2 showing an example of a dynamic 3D lung map view, according to an embodiment of the present disclosure.

FIG. 4 illustrates an example user interface that may be presented by workstation 80 showing an example view of the 3D model. User interface (UI) 400 includes a button 402 which may be used to select and/or enable the dynamic 3D lung map view. UI 400 further shows an airway tree 404, a digital probe 406, and a pathway 408.

Figure 5:
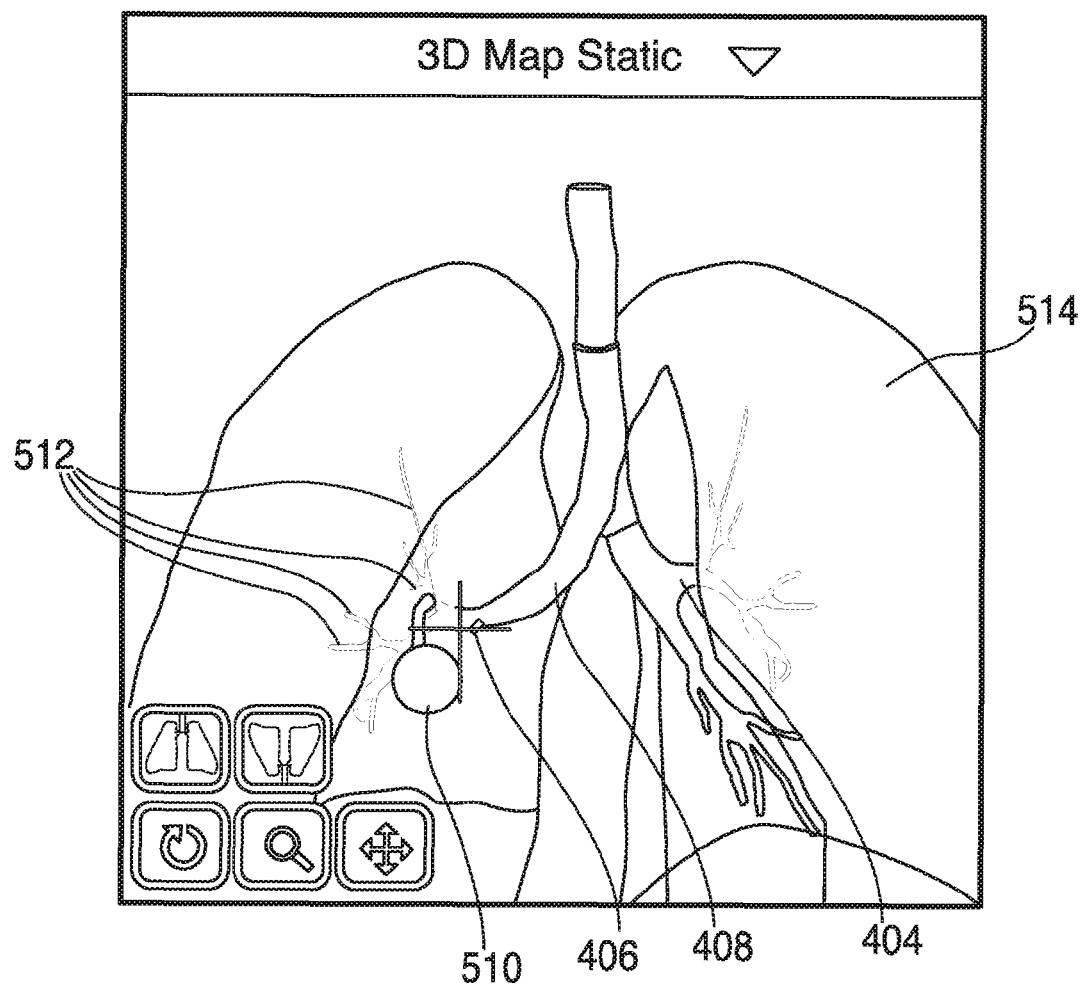
FIG. 5 illustrates an example of an unadjusted 3D lung map view, according to an embodiment of the present disclosure.

FIG. 5 illustrates an example of an unadjusted 3D lung map view which may be presented by EMN application 81 via UI 400. The unadjusted 3D lung map view shows the probe 406 within the 3D model, corresponding to the location of sensor 94 within the patient's airways. Also shown by the unadjusted 3D lung map view are the airway tree 404, the pathway 408, the target 510, the surrounding airways 512, and the pleura 514 of the lungs. The unadjusted 3D lung map view may be adjusted manually.

FIG. 6 illustrates an example view of a dynamic 3D lung map view which may be presented by EMN application 81. The example dynamic 3D lung map view shows the same probe 406 and target 510 as the unadjusted 3D lung map view of FIG. 5. However, the dynamic 3D lung map view has been adjusted by zooming in on the 3D model to show the position of probe 406 in relation to target 510. The dynamic 3D lung map view has further been aligned with the tip of probe 406, or a vector 614 from digital probe 406 to target 510, and positioned such that pathway 408 and surrounding airways 512 may clearly be seen. A line 614 indicates the line of sight from the tip of digital probe 406 intersecting with target 510.

FIG. 7 illustrates an example dynamic 3D lung map view wherein objects have been hidden or "ghosted out" to more clearly show the objects and components of the 3D model which are relevant to the current procedure, according to an embodiment of this disclosure. Hiding or "ghosting out" objects may involve completely removing such objects from the displayed 3D lung map, or such objects may be shown in a different way from objects which are not hidden, for example with a higher level of transparency. The example dynamic 3D lung map view includes airway tree 404, probe 406, pathway 408, target 510, surrounding airways 512, and vector 614, as described above with reference to FIGS. 4-6.

The example dynamic 3D lung map view further shows additional targets 718 which have been hidden because they are located outside of the region of interest, as described above with regard to step S304 of FIG. 3. The example dynamic 3D lung map view also shows that a branch 720 of airway tree 404 which overlaps with pathway 408 and target 510, and thus obstructs the view of pathway 408 and target 510, has been hidden, as described above with regard to step S308 of FIG. 3. Additionally, the example dynamic 3D lung map view shows that a target 722 which does lie within the region of interest but is not relevant to the current procedure has been hidden, as described above with regard to step S312 of FIG. 3. Target 722 may, for example, be a subsequent target on the current pathway to which the tool will be navigated during the current procedure, but it is not yet relevant to the procedure because at least one other target 510 must first be visited. The current pathway may be divided into two or more portions: a first portion 408 representing the portion of the pathway to be navigated to the current target 510, and additional portions 708 representing the portion of the pathway leading to the next target 722 to be visited. The dynamic 3D lung map view also shows that other objects, such as markers 724, are hidden because they are not relevant to the current procedure. Markers 724 may be, for example, markers indicating the locations where previous biopsies were performed.

By using the dynamic 3D lung map view described above during an ENB procedure, the clinician may be presented with a continuously updated view of the 3D model which is adjusted as the tool, and thus sensor 94, is moved through the patient's airways. The dynamic 3D lung map view presents the clinician with a view of the 3D model from a viewpoint which clearly shows digital probe 406, and removes objects which may obscure digital probe 406, airway tree 404, target 510, and/or other objects which are relevant to the ENB procedure being performed.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

With respect to memory 202 described above in connection with FIG. 2, the memory 202 may include any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Further aspects of image and data generation, management, and manipulation useable in either the planning or navigation phases of an ENB procedure are more fully described in commonly-owned U.S. Provisional Patent Application Ser. No. 62/020,177 entitled "Methods for Marking Biopsy Location", filed on Jul. 2, 2014, by Brown; U.S. Provisional Patent Application Ser. No. 62/020,238 entitled "Intelligent Display", filed on Jul. 2, 2014, by Kehat et al.; U.S. Provisional Patent Application Ser. No. 62/020,242 entitled "Unified Coordinate System for Multiple CT Scans of Patient Lungs", filed on Jul. 2, 2014, by Greenburg; U.S. Provisional Patent Application Ser. No. 62/020,245 entitled "Alignment CT", filed on Jul. 2, 2014, by Klein et al.; U.S. Provisional Patent Application Ser. No. 62/020,250 entitled "Algorithm for Fluoroscopic Pose Estimation", filed on Jul. 2, 2014, by Merlet; U.S. Provisional Patent Application Ser. No. 62/020,261 entitled "System and Method for Segmentation of Lung", filed on Jul. 2, 2014, by Markov et al.; and U.S. Provisional Patent Application Ser. No. 62/020,258 entitled "Cone View—A Method of Providing Distance and Orientation Feedback While Navigating in 3D", filed on Jul. 2, 2014, by Lachmanovich et al., the entire contents of all of which are hereby incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A non-transitory computer-readable storage medium storing a program for implementing a dynamic three-dimensional (3D) lung map view for navigating a probe inside a patient's lungs, the program including instructions which, when executed by a processor, cause a computing device to:
load a navigation plan into a navigation system, the navigation plan including a planned pathway shown in a 3D model generated from a plurality of CT images;
present guidance for inserting a probe into a patient's airways, the probe including a location sensor in operative communication with the navigation system;
register a sensed location of the probe with the planned pathway;
select a target in the navigation plan;
present a view of the 3D model showing the planned pathway and indicating the sensed location of the probe;
present guidance for navigating the probe through the airways of the patient's lungs toward the target;
iteratively adjust the presented view of the 3D model showing the planned pathway based on the sensed location of the probe; and
update the presented view by removing at least a part of an object forming part of the 3D model.

2. The non-transitory computer-readable storage medium according to claim 1, wherein iteratively adjusting the presented view of the 3D model includes zooming in when the probe approaches the target.

3. The non-transitory computer-readable storage medium according to claim 1, wherein iteratively adjusting the presented view of the 3D model includes zooming in when the diameter of an airway within which the probe is sensed to be located is less than a predetermined threshold.

4. The non-transitory computer-readable storage medium according to claim 1, wherein iteratively adjusting the presented view of the 3D model includes changing the presented view to a view wherein the airway tree bifurcation is maximally spread.

5. The non-transitory computer-readable storage medium according to claim 1, wherein iteratively adjusting the presented view of the 3D model includes aligning the view with the sensed location of the probe to show where the probe is and what lies ahead of the probe.

6. The non-transitory computer-readable storage medium according to claim 1, wherein iteratively adjusting the presented view of the 3D model includes changing the presented view to be orthogonal to a vector from the probe to the pathway.

7. The non-transitory computer-readable storage medium according to claim 1, wherein iteratively adjusting the presented view of the 3D model includes changing the presented view to be perpendicular to the sensed location of the probe in relation to the 3D model to show the area around the probe.

8. The non-transitory computer-readable storage medium according to claim 1, wherein iteratively adjusting the presented view of the 3D model includes changing the presented view to be behind the sensed location of the probe in relation to the 3D model to show the area ahead of the probe.

9. The non-transitory computer-readable storage medium according to claim 1, wherein iteratively adjusting the presented view of the 3D model includes changing the presented view to be at the tip of the probe and orthogonal to the direction in which the probe is moving.

10. The non-transitory computer-readable storage medium according to claim 1, wherein iteratively adjusting the presented view of the 3D model includes changing the presented view to be perpendicular to a vector from the probe to the target to show the alignment of the probe to the target.

11. The non-transitory computer-readable storage medium according to claim 1, wherein iteratively adjusting the presented view of the 3D model includes rotating the presented view around a focal point to improve a 3D perception of the sensed location of the probe in relation to the 3D model.

12. The non-transitory computer-readable storage medium according to claim 1, wherein updating the presented view by removing at least part of an object includes removing at least part of an object which is outside of a region of interest.

13. The non-transitory computer-readable storage medium according to claim 1, wherein updating the presented view by removing at least part of an object includes removing at least part of an object which is obstructing the probe.

14. The non-transitory computer-readable storage medium according to claim 1, wherein updating the presented view by removing at least part of an object includes removing at least part of an object which is obstructing the target.

15. The non-transitory computer-readable storage medium according to claim 1, wherein updating the presented view by removing at least part of an object includes removing at least part of an object which is not relevant to the sensed location of the probe.

16. The non-transitory computer-readable storage medium according to claim 1, wherein updating the presented view by removing at least part of an object includes removing at least part of an object which is not relevant to a current selected state of the navigation system.

17. The non-transitory computer-readable storage medium according to claim 1, wherein the instructions, when executed by the processor, further cause the computing device to present an alert.

18. The non-transitory computer-readable storage medium according to claim 17, wherein presenting an alert includes presenting an alert when the probe is approaching the pleura.

19. The non-transitory computer-readable storage medium according to claim 17, wherein presenting an alert includes presenting an alert when the tool is approaching major blood vessels.

20. The non-transitory computer-readable storage medium according to claim 17, wherein presenting an alert includes presenting an alert when the sensed location of the probe is off of the planned pathway.

* * * * *